United States Patent [19]
Brinkman et al.

[11] Patent Number: 5,476,932
[45] Date of Patent: Dec. 19, 1995

[54] PROCESS FOR PRODUCING N4-ACYL-5'-DEOXY-5-FLUOROCYTIDINE DERIVATIVES

[75] Inventors: Herbert R. Brinkman, Bushkill, Pa.; Panayiotis Kalaritis, New Providence; John F. Morrissey, Belleville, both of N.J.

[73] Assignee: Hoffmann-La Roche Inc., Nutley, N.J.

[21] Appl. No.: 296,842

[22] Filed: Aug. 26, 1994

[51] Int. Cl.$^6$ .......................... C07H 1/00; C07H 19/067
[52] U.S. Cl. ........................ 536/55.3; 536/28.53
[58] Field of Search ................ 536/27.11, 55.3, 536/28.53

[56] References Cited

U.S. PATENT DOCUMENTS 4,966,891  10/1990  Fujiu et al. .................. 514/49

OTHER PUBLICATIONS

Ninomiya et al, Jpn. J. Cancer Res. 81: 188–195, 1990.
Bloom et al. Nucl. Acids Res. 4(4): 1047–1063, 1977.

Primary Examiner—Gary L. Kunz
Attorney, Agent, or Firm—George M. Gould; William H. Epstein; Catherine A. Picut

[57] ABSTRACT

A process for preparing N4-acyl-5'-deoxy-5-fluorocytidine derivatives of formula III:

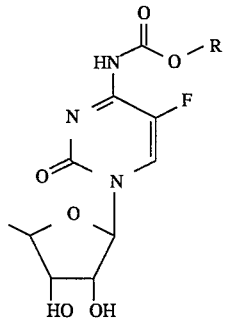

by selective deacylation, wherein R is alkyl, cycloalkyl, alkenyl, aralkyl or aryl,
which comprises reacting a compound of formula II,

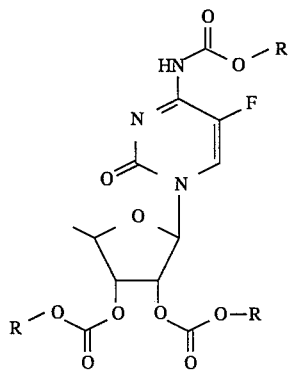

wherein R is as defined above,
with a base in an aqueous or inert organic solvent.

5 Claims, No Drawings

PROCESS FOR PRODUCING N4-ACYL-5'-DEOXY-5-FLUOROCYTIDINE DERIVATIVES

BACKGROUND OF THE INVENTION $N^4$-Acyl-5'-fluorocytidine derivatives of the formula:

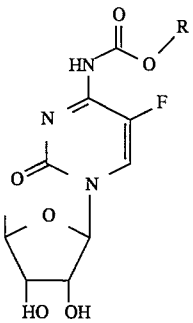

wherein R is alkyl, cycloalkyl, alkenyl, aralkyl, aryl. are known compounds having anti-tumor activity [Japanese Journal of Cancer Research, Vol. 81, pp. 188–195 (1990)]:

These compounds may be produced starting from 5'-deoxy-5-fluorocytidine as described in Japanese Patent Application Kokai No. 153,696/1989.

This process is time-consuming and difficult to perform on a commercial scale, and involves the sequential steps of introducing a protective acyl group in the hydroxy radicals of the sugar part of this compound, introducing an acyl group into the amino radical of this compound, and thereafter eliminating the acyl groups from the sugar part.

A process for deacylating the sugar part of these acylcytidine derivatives has been described [J. H. van Bloom et al, Nucleic Acids Research, vol 4 (4), pp. 1047–63 (1977)]. Generally it is known that acyls on the sugar part are eliminated when acylcytidine derivatives react with an alkali. However, removal of the acyl from the amino group also takes place, so that complicated operations of separation and purification are required in order to obtain the $N^4$-acyl-5'-deoxy-5-fluorocytidine derivatives containing only the acyl attached to the amino group.

SUMMARY OF THE INVENTION

This invention provides a novel process for producing derivatives of the known anti-tumor agent $N^4$-acyl-5'-deoxy-5-fluorocytidine of formula III,

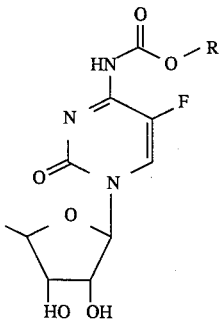

wherein R is alkyl, cycloalkyl, alkenyl, aralkyl or aryl.

Said process utilizes as an intermediate the novel compound of formula II,

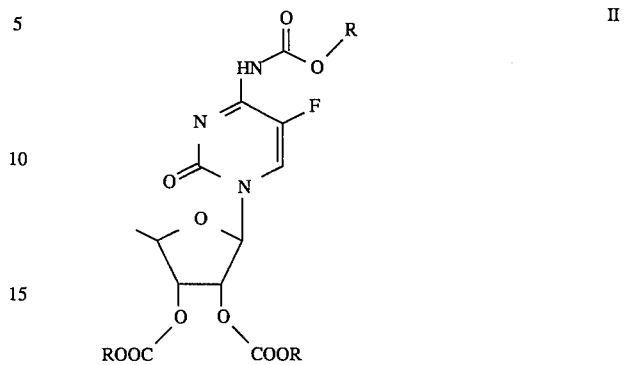

wherein R is as above, and provides for selective elimination of only the carbonyl COOR radical from its hydroxy sugar part. Because of the step of selective hydrolysis, $N^4$-acyl-5'-deoxy-5-fluorocytidine derivatives can be produced by a simpler process in a few chemical steps and in excellent yields of up to 80% from the compound of formula II. An overall yield of $N^4$-acyl-5'-deoxy-fluorocytidine of 62% from 5-fluorocytosine can be obtained by this process.

DETAILED DESCRIPTION OF THE INVENTION

A process for producing $N^4$-acyl-5'-deoxy-5-fluorocytidine derivatives of formula III is provided firstly:

A process for producing $N^4$-acyl-5'-deoxy-5-fluorocytidine derivatives of the formula III

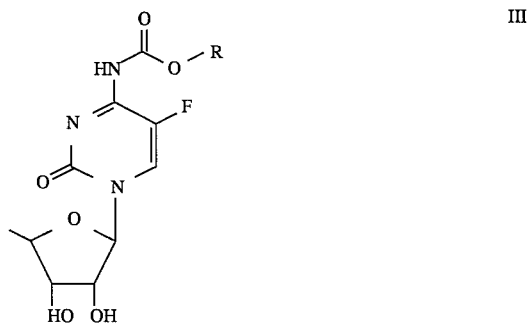

wherein R is alkyl, cycloalkyl, alkenyl, aralkyl or aryl, is prepared by treating a compound of formula II

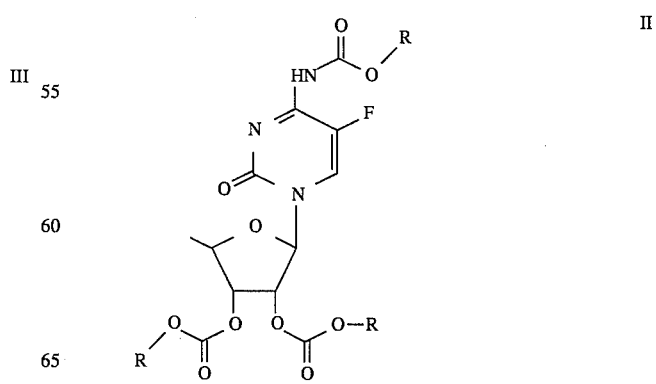

wherein R is as above, with an organic or inorganic base in an aqueous or inert organic solvent to selectively hydrolyze the carbonyl (COOR) group from the sugar part of this compound of formula II.

In carrying out the above reaction, the reaction temperature is not critical and may be within the range of −30° C. to +20° C. The temperature preferably is within the range of from about −10° C. to about +10° C. Best results are obtained at 0° C. The inert solvent may be any aqueous or inert organic solvent which is water miscible. The preferred solvents are water; alcohols selected from the group consisting of methanol, ethanol, propanol, butanol, isopropanol; ethers, such as tetrahydrofuran; dioxane; acetones; acid amides, such as dimethyl formamide; carbon halogenides, such as methylene chloride, chloroform, etc.; aromatic hydrocarbons, such as toluene, xylene, etc; and mixtures or combinations thereof.

When a mixture of solvents are used, the reaction may be carried out by adding a phase transfer catalyst.

An organic or inorganic base may be used to convert a compound of formula II in the compound of formula III. Examples of organic bases includes alkali metal alkoxides, triethylamine, 1,8-diazabicyclo (5.4.0 undec-7-ene) (known as DBU), N-methyl morpholine and pyridine. The preferred organic base is an alkali metal alkoxide, such as sodium methoxide. Examples of inorganic bases include ammonium hydroxide and sodium hydroxide. The preferred inorganic base is sodium hydroxide. The quantity of base used to convert formula II to formula III is not critical. The quantity of base used to selectively hydrolyze the carbonyl group from the sugar part of compound of formula II is within the range of from about two (2) to about six (6) mole equivalents to the quantity of compound of formula II. The preferred amount of base is four (4) mole equivalents.

R can be any alkyl, cycloalkyl, alkenyl, aralkyl or aryl group. When R is alkyl, R can be any straight or branched chain alkyl group having 1–22 carbon atoms. The preferred alkyl groups are lower alkyl containing 1 to 6 carbon atoms, such as methyl, ethyl, propyl, isopropyl, butyl, isobutyl, pentyl or the like.

When R is cycloalkyl, it includes any cycloalkyl containing 3 to 12 carbon atoms, such as cyclopropyl, cyclobutyl, cyclopentyl, cyclohexyl, adamantyl, or the like.

When R is alkenyl it can be any substituted and unsubstituted alkenyl radical containing 2–22 carbon atoms. When R is alkenyl, lower alkenyl containing 1 to 6 carbon atoms is preferred. The preferred lower alkenyl groups are alyl, 1-propyl, butenyl, pentenyl and hexenyl. When R is substituted alkenyl, the preferably substitution groups are lower alkyl or aryl.

When R is aryl, aryl may be substituted or unsubstituted. The term aryl signifies mononuclear aromatic hydrocarbon groups such as phenyl, and polynuclear aryl groups such as napthyl, anthryl, phenanthryl, etc. The mononuclear and polynuclear aryl groups can be substituted in one or more positions. When R is unsubstituted mononuclear aryl, phenyl is enumerated. When R is substituted mononuclear aryl, the preferred substitution groups are lower alkyl containing 1 to 6 carbon atoms, halo, lower alkoxy, nitro, cyano, acetyl, carbamoyl, and lower alkoxycarbanoyl.

The aryl groups may contain heteroatoms, wherein the heteroatoms are selected from the group consisting of nitrogen, oxygen, or sulfur. These heteroaryls can be unsubstituted or substituted with the above mentioned substitutions.

When R is mononuclear heteroaryl, then R may be thienyl, methylthienyl, furyl, nitrofuryl, etc.

The preferred polynuclear aryl groups include napthyl, biphenylyl, pyrrolyl, methylpryrrolyl, imidazolyl, pyrazolyl, pyridyl, methylpyridyl, pyrazinyl or the like.

When R is aralkyl, aralkyl denotes aryl lower alkyl groups, wherein aryl is defined as above and lower alkyl contains 1 to 6 carbon atoms. The aryl group can be unsubstituted or substituted with the substituents described with respect to aryl above. The preferred unsubstituted aralkyl groups include benzyl and 1 phenylethyl. The substituted aralkyls include methylbenzyl, fluorobenzyl, chlorobenzyl, methoxybenzyl, dimethoxybenzyl, nitrobenzyl, phenethyl, picolyl, 3-indolylmethyl or the like.

After completion of reaction, the compound of the formula III is obtained in isolated and pure form using a combination of conventional separation and purification methods.

In accordance with this invention, the compound of formula II can be produced by treating 5'-deoxy-5-fluorocytidine of formula I,

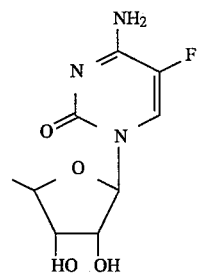

with a compound of formula

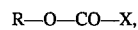

R—O—CO—X, wherein R is as above and X is a reactive group, in an inert organic solvent in the presence of an organic base. X can be any reactive group such as a halide, anhydride, mixed anhydride, sulfated alkyl, e.g. mesyl, or sulfated aryl, e.g. tosyl. When X is a halide, any halide may be used such as bromine, fluorine or chlorine. The preferred halide is chlorine.

The reaction temperature for the above reaction is not critical. The temperature range may be from about −30° C. to about +20 ° C., preferably from about −10° C. to about +10° C. Best results are obtained at temperatures at about 0° C.

The solvent may be any inert organic solvent polar or non-polar, such as dimethylformamide, acetonitrile, toluene, chloroform, pyridine, lutidine or dimethyl sulfoxide; or a halogenated hydrocarbon, such as dichloromethane. The preferred organic solvent is dichloromethane. Any organic base may be used, such as triethylamine, tributylamine, pyridine, N,N-dimethylaminopyridine, lutidine, N-methylmorpholine, etc. The preferred organic base is pyridine.

5'-deoxy-5-fluorocytidine as a starting substance for the above reaction is a known compound [J. Med. Chem., 22 1330 (1979)] and is produced by known means, for example, from 5-fluorocytosine through 5-fluorocytidine [Chem Pharm. Bull., vol 26, No. 10 2990 (1978)]. [U.S. Pat. No. 4,966,891] (cf. Japanese Patent Publication No. 34,479/ 1983), or from 5'-deoxy-5-fluorouridine by the procedures described in the literature [Chem. Pharm. Bull., 33, 2575 (1985)].

The compounds of formula II are novel compounds.

Hereinafter, the following typical compound of formula II will be exemplified.

-5'-deoxy-2',3'-di-O-n-pentyloxycarbonyl-5-fluoro-$N^4$-n-pentyloxycarbonylcytidine.

-5'-deoxy-2',3'-di-O-n-butyloxycarbonyl-5-fluoro-$N^4$-n-butyloxycarbonylcytidine.

EXAMPLES

Example 1

5'-deoxy-2',3'-di-O-n-pentyl-oxycarbonyl-5-fluoro-$N^4$-n-pentyloxycarbonylcytidine (Formula II)

A 500 ml roundbottomed jacketed flask was inerted, cooled to −10° C. and charged with 125 mls. dichloromethane, 50 mls. chloropentylformate (0.33 moles) and 30 mls. pyridine (0.38 moles) while maintaining the reaction temperature at or below −10° C.

With the aid of a powder addition funnel, 24.5 grams of 5'deoxy-5-fluorocytidine was added over 45 minutes, while maintaining the temperature below −5° C. The solid was seen to dissolve readily initially, while dissolution became less evident toward the latter part of the addition. A slight exotherm was controlled by the cooling system. The reaction mixture was allowed to stir overnight at 0° C.

The suspended solids were filtered and the wet cake washed three times, each with 5 mls of dichloromethane. The water soluble cake was determined to be C5H5N HCl. The filtrate was stripped to dryness on a rotavap at 40° C. and 20 mmHg. The residue was dissolved in 75 mls. ethyl acetate and the insoluble material filtered off. The cake was washed three times with 25 mls each of ethyl acetate, where the wash liquors were combined with the filtrate. The solution was stripped to dryness to produce 50.55 grams of 5'-deoxy-2',3'-di-O-n-pentyl-oxycarbonyl-5-fluoro-$N^4$-n-pentyloxycarbonylcytidine which represents a yield of 92% from the 24.5 grams starting material.

Example 2

Producing
5'-deoxy-5-fluoro-$N^4$-n-pentyloxycarbonyl-cytidine
(Formula III)

The residue from Example 1 (i.e., 50.55 grams of 5'-deoxy-2',3'di-O-n-pentyloxycarbonyl-5-fluoro-$N^4$-n-pentyloxycarbonyl cytidine) was dissolved in 50 mls. methanol and chilled to −10° C. Sixteen (16) grams of sodium hydroxide dissolved in 22 mls double distilled water was added over 30 minutes to the residue solvent while maintaining the temperature below −10° C. The solution was agitated for 15 minutes and the reaction checked for completion. Upon completion, 32 mls of concentrated hydrogen chloride 37% was added to reduce the pH of the reaction mixture to between 4.5 and 5.5.

250 mls of dichloromethane was added to the slurry along with 50 mls water, the mixture agitated for 15 minutes and the lower organic phase split off. This phase was washed with 50 mls water, the aqueous layers combined and back washed with 70 mls dichloromethane. The product streams were combined and stripped to dryness. The material obtained was 5'-deoxy-5-fluoro-$N^4$-n-pentyloxycarbonylcytidine. The crude weight of material obtained was 40.45 grams; which represents a yield of 113% from the 50.55 grams of starting material of formula II.

Example 3

Purification of
5'-deoxy-5,fluoro-$N^4$-n-pentyloxycarbonyl cytidine
(Formula III)

To purify the 40.45 grams of 5'-deoxy-5-fluoro-$N^4$-n-pentyloxycarbonyl cytidine obtained from Example 2, the residue from Example 2 was dissolved in 125 mls ethyl acetate with vigorous agitation. Product precipitation occurred almost immediately. When all the crude material had been dissolved the slurry was cooled to 0° C. and aged for 1 hour. The crystals were recovered and washed twice with 20 mls. each hexane ethyl acetate (50/50 ice cold mixture) and the ultra white product was dried overnight at 40° C., with 5 mm Hg vacuum. The yield was 28.7 g. equivalent to an overall yield of 80% based on the 24.5 grams of 5'-deoxy-5-fluorocytidine.

Example 4

Producing
5'-deoxy-2',3'di-O-n-butyloxycarbonyl-5-fluoro-$N^4$-n-butyloxycarbonylcytidine (Formula II)

A 500 ml roundbottomed jacketed flask was inerted, cooled to 20° C. and charged with 120 mls pyridine (148 moles) and 5'-deoxy-5-fluorocytidine (36.1 gm). With the aid of an addition funnel, n-butylchloroformate (66.4 gm) was added over 1 hour, while maintaining the temperature below 20° C. The reaction mixture was allowed to stir for 2 hours at 20° C.

The reaction mixture was stripped to dryness on a rotovap at 40° C. and 20 mmHg. The residue was dissolved in 225 mls of ethyl acetate and washed with 120 mls water. The organic phase was separated and washed with 165 mls 10% aqueous HCL followed by eleven (11) mls saturated $NaHCO_3$.

The ethyl acetate layer was collected and stripped to dryness. The material obtained was 5'-deoxy-2',3'-di-O-n-butyloxycarbonyl-5-fluoro-$N^4$-n-butyloxycarbonylcytidine. The crude weight of material obtained was 63.0 grams, which represent a yield of 85%.

Example 5

Producing
5'-deoxy-5-fluoro-$N^4$-n-butyloxycarbonylcytidine
Formula III

The residue from Example 1 (i.e., 63.0 grams of 5'-deoxy-2',3'-di-O-n-butyloxycarbonyl-5-fluoro-$N^4$-butyloxycarbonyl cytidine) was dissolved in 125 mls methanol and chilled to 0° C. A 50% aqueous NaOH solution was added over 30 minutes while maintaining the temperature at 0° C.

The solution was agitated for 2 hours and the reaction checked for completion. Upon completion, 12 mls of concentrated hydrogen chloride (37%) was added to reduce the pH to 4.5.

Dichloromethane (150 mls) was added to the slurry along with 150 mls water, the mixture agitated for 15 minutes and the lower organic layer split off this phase was washed with 150 mls saturated $NaHCO_3$. The organic layer was separated and concentrated to dryness. The material obtained was 5'-deoxy-5 -fluoro-$N^4$-n-butyloxycarbonylcytidine. The crude weight of material obtained was 30.5 gm; which represents a yield of 72%.

We claim:

1. A process for producing N4-acyl-5'-deoxy-5 -fluorocytidine derivatives of formula III:

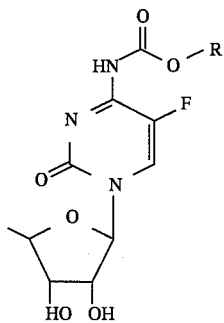

III wherein R is alkyl, cycloalkyl, alkenyl, aralkyl or aryl, which comprises treating a compound of formula II:

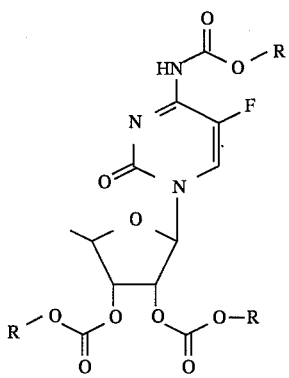

II wherein R is as above,
in an aqueous or inert organic solvent, in a base selected from the group consisting of an alkali metal alkoxide, triethylamine, 1,8-diazabicyclo (5.4.0 undec-7-ene), N-methyl morpholine, pyridine, ammonium hydroxide and sodium hydroxide, to produce said fluorocytidine derivatives of formula III.

2. A process of claim 1, wherein said treating is carried out at a temperature from about −10° C. to about 10° C.

3. A process of claim 1, wherein said treating is carried out at a temperature about 0° C.

4. A process of claim 1, wherein said solvent is water.

5. A process of claim 1, wherein said base is sodium hydroxide and said solvent is methanol.

* * * * *